United States Patent [19]

Kenkare et al.

[11] 4,113,852

[45] *Sep. 12, 1978

[54] ANTIPERSPIRANT COMPOSITION

[75] Inventors: Divaker B. Kenkare, South Plainfield; Durland K. Shumway, Piscataway, both of N.J.

[73] Assignee: Colgate-Palmolive Company, New York, N.Y.

[*] Notice: The portion of the term of this patent subsequent to Aug. 22, 1995, has been disclaimed.

[21] Appl. No.: 557,561

[22] Filed: Mar. 12, 1975

[51] Int. Cl.² .............................................. A61K 7/38
[52] U.S. Cl. ...................................... 424/46; 424/47; 424/68
[58] Field of Search .......................... 424/68, 46, 47

[56] References Cited

U.S. PATENT DOCUMENTS

3,873,686  3/1975  Beekman ................................ 424/47

FOREIGN PATENT DOCUMENTS

770,007  3/1957  United Kingdom ...................... 424/68
1,347,950  2/1974  United Kingdom ...................... 424/47

*Primary Examiner*—Dale R. Ore
*Attorney, Agent, or Firm*—H. S. Sylvester; M. M. Grill; N. Blumenkopf

[57] ABSTRACT

An improved antiperspirant composition is prepared by spray drying together a mixture of aluminum chloride, aluminum chlorhydrate, and urea. The impalpable powder which is formed is incorporated into an aerosol antiperspirant formulation.

7 Claims, No Drawings

ANTIPERSPIRANT COMPOSITION

BACKGROUND OF THE INVENTION

The present invention relates to antiperspirant compositons and, more particularly, to antiperspirant formulations suitable for aerosol application.

It is well known in the art to provide an antiperspirant formulation in the form of a cream, a stick, or a roll-on. However, these products have certain disadvantages, as they may leave an undesirable feel on the skin and may contain an excessive quantity of alcohol and water. More recently, aerosols under pressure have become popular as a convenient form for application of antiperspirant formulations to the skin. Aerosol antiperspirant and deodorant products not occupy a majority of the market for antiperspirant and deodorant products.

An aerosol product which possesses the attractive cosmetic properties and convenience benefits of currently available aerosol deodorant products and which additionally possesses substantial antiperspirant effects without excessive skin irritation would be highly desirable. Since the known inorganic astringent salts possess far greater antiperspirant activity than the organic astringent salts heretofore suggested for aerosol use, the inorganic salts must be used, despite the formulation problems involved, to provide such a product.

Among the most effective astringent inorganic salts are aluminum chloride and aluminum chlorhydrate. Aluminum chlorhydrate, also known as aluminum chlorhydroxide complex or basic aluminum chloride, has an approximate atomic ratio of aluminum to chlorine of 2:1, e.g., 2.1:1 to 1.9:1, and an empirical formula of $Al_2(OH)_5Cl$, existing as a hydrate in solid form.

The efficacy of an antiperspirant composition is largely dependent upon the relative activity of the astringent salt employed therein. However, skin irritation can result from the low pH of many conventional antiperspirant formulations. It has been found that urea is very effective in reducing skin irritation caused by these formulations without reducing their efficacy. However, the large particle size and hygroscopicity of urea so far has prevented its use in dry aerosol antiperspirant products.

Accordingly, it is a primary object of this invention to provide improved aerosol antiperspirant compositions.

It is a further object of this invention to provide a dry aerosol antiperspirant formulation which may be applied in powder form, exhibits a high degree of antiperspirant activity and minimizes skin irritation.

It is a more specific object of this invention to provide dry aerosol antiperspirant formulations having desirable spray characteristics, relative freedom from valve clogging, and which contain highly effective levels of inorganic astringent salts while minimizing skin irritation.

SUMMARY OF THE INVENTION

It has now been discovered that these and other objects are achieved by an aerosol antiperspirant composition, which comprises an impalpable powder formed by co-spray drying together solutions of aluminum chloride, aluminum chlorhydrate, and urea. The optimum compositions include from about 78% to about 92% aluminum chlorhydrate, from about 6% to about 12% aluminum chloride, and from about 1% to about 10% urea. It is preferred to use from about 85% to about 90% aluminum chlorhydrate, from about 8% to about 12% aluminum chloride, and from about 2% to about 7% urea.

Antiperspirant formulations can be readily prepared from the antiperspirant compositions of the present invention by adding to the antiperspirant compositions the usual cosmetically acceptable adjuvants and propellants. Typically, a suspending agent is used to keep the antiperspirant composition from agglomerating or settling out and packing tightly at the bottom of the aerosol container. A carrier is added so that the stream issuing from the aerosol container is a moist spray which effectively adheres to the skin rather than a dusty cloud which does not adhere as well. A propellant is added to force the antiperspirant formulation out of the container. The preferred propellants are n-butane and the Freon series of hydrocarbons. Minor adjuncts such as antimicrobial compounds and perfumes are optional.

It has been found that the antiperspirant compositions of the present invention are particularly well suited for powder type antiperspirant formulations. In such cases it is sometimes desirable to add from about 1% to about 5% by weight of talc or other suitable powder to the formulation.

In these formulations the antiperspirant composition is present in amounts ranging from about 2% to about 15% by weight and most preferably in amounts ranging from about 3% to about 8% by weight. Below about 2%, the antiperspirant effectiveness falls off. Amounts above about 15% are not practical economically because the antiperspirant effectiveness does not increase commensurate with additional quantites used, in addition to causing handling and atomization problems.

An important component of the subject composition is a cosmetically acceptable non-volatile, propellant-soluble vehicle. Examples of such compounds are fatty acid esters, fatty alcohols, hydrocarbons such as mineral oil, lanolin and its derivatives, silicone oils such as dimethyl polysiloxane, diesters of dibasic acids, and non-ionic vehicles such as the esters and partial esters of fatty acids containing from 6 to 22 carbon atoms. Useful vehicles include but are not limited to isopropyl palmitate, isopropyl myristate, ethylene glycol, butyl stearate, glyceryl trioleate, stearyl palmitate, diethylene glycol, triethylene glycol, tetraethylene glycol, trimethylol propane, propylene glycol, 1,4-hexanediol, 1,2,6-hexanetriol, dipropylene glycol, di-n-octyl-n-decyl phthalate, di-n-butyl phthalate, di-n-hexyl phthalate, di-n-octyl phthalate, diethyl sebacate, diisopropyl adipate, dimethyl phthalate, glycerine, ethoxylated lanolin, acetylated lanolin, propylene glycol dipelargonate, 1,3-butanediol, 2-methyl-2-ethyl-1,3-propanediol, ethylene glycol ethyl ether, ethylene glycol methyl ether, diethylene glycol methyl ether, diethylene glycol ethyl ether, 2-methyl-2,4-pentanediol, 1,4-butanediol, 1,2,4-butanetriol, diglycerol, oleyl alcohol, cetyl alcohol, lauryl alcohol, and mixtures of the above.

Another important component of the subject composition is a suspending agent. Useful materials for inclusion in the subject composition are known bulking agent compounds such as: a colloidal silica such as "Cab-O-Sil", , a pyrogenic silica having a particle diameter between about 0.001 and 0.03 microns; colloidal (fumed) alumina; finely divided hydrophobically treated clays such as a reaction product of a clay such as bentonite or hectorite with, for example, dimethyldistearyl ammonium chloride; colloidal magnesium aluminum silicates; other montmorillonite clays; and hydrophobically treated montmorillonite clays.

The preferred suspending agents are the hydrophobically treated montmorillonite or hectorite clays available under the trademark "Bentone" which are prepared by reacting a clay such as bentonite or hectorite in a cation exchange system with a variety of amines. Different amines are reacted to obtain different Bentone suspending agents which may also differ in proportions of $SiO_2$, $MgO$ and $Al_2O_3$. Examples of useful Bentone suspending agents are Bentone-27, which is a stearaluminum hectorite; Bentone-34, which is quaternium 18 bentonite; Betone-38, which is quaternium 18 hectorite; and Bentone-14, which is a clay extended quaternium 18 hectorite, all of which have a particle size of below about 5 microns and are commercially available from the NL Industires, Inc.

The hydrophobic clays should be thoroughly dispersed. Three forms of energy which aid in such dispersion are temperature increase, chemical energy and mechanical shearing action. Chemical energy can be supplied in the form of a polar additive such as alcohol or a high boiling organic liquid such as propylene carbonate. Propylene carbonate, usually in an amount of about 0.05 to about 0.5%, is also particularly helpful when the organic liquid has poor wetting properties, or when dispersion is unusually difficult. As taught by NL Industries in their Data Sheet B-33 of April 1970, high mechanical shearing action is also an important factor. Equipment such as homogenizers, shear pumps, and colloid mills will give positive results. Examples of useful mixers include, among others, the Cowles Dissolver and the Eppenbach Homogenizer.

The propellant used in connection with the subject invention may be any liquifiable propellant suitable for use in connection with the dispensing of the solid material. That is to say any non-toxic, volatile, organic material which exists as a gas at the temperature of use (and ambient or atmospheric pressure) and which exists as a liquid at the same temperature under superatmospheric pressures, can be used as the gas-producing agent. Especially suitable are the $C_3$-$C_4$ aliphatic hydrocarbons, namely, liquefied propane, n-butane, isobutane, isobutylene; halogenated aliphatic hydrocarbons which contain from 1 to 2 carbon atoms and include, by way of example, methylene chloride, "Freons" such as dichlorodifluoromethane, monochlorodifluoromethane, dichlorotetrafluoroethane, trichlorofluoromethane, trichlorofluoroethane, difluoroethane, difluoromonochlorethane, trichlorotrifluoroethane, monofluorodichloromethane, monofluorodichloroethane, pentafluoromonochloroethane; cyclic hexafluorodichlorobutane, octafluoropropane; and cyclic octafluorobutane, and mixtures of the two or more thereof. Preferably the saturated hydrocarbons and halogenated saturated aliphatic hydrocarbons are employed in the subject composition. The preferred propellant for use in connection with the subject composition is a mixture of dichlorodifluoromethane and trichloromonofluoromethane in a 35:65 blend.

In addition to the essential components of the subject composition one may also include therein components such as perfumes, colorings, and the like, so as to improve the aesthetic value and consumer acceptability thereof.

Although not essential for this invention, it is desirable to add a non-irritating, non-toxic germicide or bactericide in amounts of about 0.02 to .5% by weight of the total composition. Suitable antiseptic agents include dichlorophene, 3, 4',5 tribromosalicylanilide; 2, 2', 3, 4-tetrabromosalicylanilide, and other bacteriostats commonly known in the market as well as mixtures thereof.

The proportional amounts of each component herein is important to the acceptability of the final composition. Therefore, one should incorporate said nonvolatile, propellantsoluble vehicle in amounts of from about 0.5 to about 15% with the preferred range being from about 1.5 to about 8% of the total composition. The suspending agent is employed in amounts of from about 0.1 to about 3%, desirably about 0.1 to 1% and, preferably incorporating from about 0.25 to about 0.5% thereof with the remainder (normally about 65 to 95%, preferably about 80 to 95%) of the composition being comprised of the propellant therefore. As already mentioned, small amounts of perfume and of coloring may be added.

It will be understood that other ingredients may be added to the above composition in minor proportions without affecting the nature of the invention.

DESCRIPTION OF THE PREFERRED EMBODIMENTS

EXAMPLE I

A powdered antiperspirant was prepared from the following starting materials:

|  | % by weight |
|---|---|
| Aluminum chlorhydrate aqueous solution (50% $Al_2(OH)_5Cl$) | 87.7 |
| Aluminum chloride aqueous solution (29% $AlCl_3$, balance water) | 9.8 |
| Urea | 2.5 |

The above ingredients were blended in a glass-lined vessel in the order given with minimal mechanical agitation needed to solubilize the urea. The liquid blend yielded an atomic ratio on a theoretical basis of Al:Cl or about 1.6:1.

The ingredients were spray dried in a KomlineSanderson "Little Giant" spray dryer, which had a drying chamber three feet in diameter with a three feet cylinder height and a 60° conical bottom. Heat was supplied by three direct-fired gas burners. Atomization was accomplished with a two-fluid atomizer.

The liquid mixture can be fed into the spray dryer at any temperture, although the temperature preferably ranges from about 55° F. to about 80° F. The viscosity of the feed is less than 500 cps., and the feed rate can vary from about 50 ml/minute to about 200 ml/minute. The inlet air temperature ranges from about 350° F. to about 410° F., and the outlet air temperature ranges from about 160° F. to about 210° F. The air pressure ranges from about 60 psi to about 200 psi; the feed pressure is less than 10 psi.

Larger amounts of the antiperspirant composition can be prepared in a gas-fired, cone-bottom spray dryer having a diameter of twelve feet and a height of ten feet on the straight side. In this instance the inlet air temperature ranges from about 400°-410° F. and the outlet air temperture ranges from about 195°-210° F. The air pressure is about 70 psi, and the feed rate of liquid is approximately 125-150 gallons per hour.

The oven loss of the resulting product as measured at 105° C. for 16 hours indicates a ratio of about 10-12%, and the product is micronized to a particle size of 100% through 325 mesh using a rotor/stator micronizing mill.

EXAMPLES II AND III

Additional antiperspirant compositions can be prepared in the manner of Example I from the following ingredients, given in parts by weight:

|  | II | III |
|---|---|---|
| Aluminum chlorhydrate solution (50% aqueous solution) | 80 | 85 |
| Aluminum chloride solution (28–30% aqueous solution) | 20 | 15 |
| Urea | 2.6 | 2.6 |

EXAMPLE IV

The method of EXAMPLE I was used to prepare a dry powder having the following analysis expressed as percent by weight:

| $Al_2(OH)_5Cl$ | 88.93 |
|---|---|
| $AlCl_3$ | 5.93 |
| Urea | 5.14 |
| Al:Cl ratio | 1.61:1 |

All of the above spray dried powders are micronized to a particle size of 100% through 325 mesh utilizing a rotor/stator micronizing mill.

EXAMPLE V

A high-oil type aerosol antiperspirant formulation was prepared, using the powder produced by EXAMPLE IV. The resulting formulation contained the following ingredients:

|  | % by weight |
|---|---|
| Blend of Aluminum chlorhydrate, Aluminum chloride, and Urea | 6.32 |
| Isopropyl palmitate | 6.42 |
| Bentone 38* | 0.29 |
| Propylene carbonate | 0.09 |
| Zinc stearate | 0.15 |
| Perfume | 0.20 |
| Propellant - 18% Trichloromonofluoromethane (Freon 11), 10% Dichlorodifluoromethane (Freon 12), 50% Dichlorotetrafluoroethane (Freon 114), 22% n-butane | 86.53 |

*National Lead Co. - organically modified montmorillonite clay (quaternium 18 bentonite)

The Bentone 38 was dispersed in the isopropyl palmitate under mild stirring conditions. The stirring speed was increased to high shear, and the propylene carbonate was slowly added to form a gel. Slow stirring was resumed, and the remaining ingredients, except for the propellant, were added. The propellant was added when the antiperspirant formulation was packaged in an aerosol container.

EXAMPLE VI

Following the method of EXAMPLE V, an aerosol antiperspirant formulation was prepared from the following ingredients:

|  | % by weight |
|---|---|
| blend { Aluminum chlorhydrate | 5.42 |
| Aluminum chloride | 0.60 |
| Urea | 0.30 |
| Fluid E-370 (Union Carbide)* | 2.42 |
| Bentone 38 | 0.25 |
| Propylene carbonate | 0.08 |
| Ceraphyl 41** | 0.80 |
| Zinc stearate | 0.15 |
| Perfume | 0.15 |
| Propellant (65% Freon 11, 35% Freon 12) | 89.83 |

*di-2-ethyl hexyl adipate
**linear alcohol lactate

In this example, the Bentone 38 was blended into the Fluid E-370 under mild stirring conditions before increasing the stirring speed to add the propylene carbonate.

EXAMPLE VII

A powder antiperspirant formulation was prepared using the impalpable powder of EXAMPLE I, and including the following ingredients:

|  | % by weight |
|---|---|
| Blend of Aluminum chlorhydrate, Aluminum chloride, and Urea | 6.32 |
| Isopropyl palmitate | 1.50 |
| Bentone 38 | 0.29 |
| Propylene carbonate | 0.10 |
| Zinc stearate | 0.15 |
| Perfume | 0.20 |
| Propellant (65% Freon 11, 35% Freon 12) | 91.44 |

The above formulation was tested for sweat reduction as described supra, and the results tabulated below:

| Days of Product Use | Sweat Reduction |
|---|---|
| 7 | 45.51% |
| 14 | 45.20% |

EXAMPLE VIII

A powder type antiperspirant formulation was prepared using the following ingredients, including the impalpable powder of EXAMPLE III:

|  | % by weight |
|---|---|
| blend { Aluminum chlorhydrate | 5.42 |
| Aluminum chloride | 0.60 |
| Urea | 0.30 |
| Dow Silicone 225 (dimethyl polysiloxane) | 0.75 |
| Ceraphyl 41 | 0.75 |
| Zinc stearate | 0.15 |
| Bentone 27* | 0.16 |
| Propylene carbonate | 0.06 |
| Perfume | 0.20 |
| Propellant (65% Freon 11, 35% Freon 12) | 91.61 |

*National Lead Co. - organically modified montmorillonite clay (stearaluminum hectorite)

The Bentone 27 was dispersed in the Dow Silicone 225 under mild stirring conditions. Stirring speed was increased to high shear, and the propylene carbonate was added slowly to form a gel. The remaining ingredients, except the propellant, were then combined with the gel, and the propellant was added at the time the antiperspirant formulation was packaged in an aerosol container.

EXAMPLE IX

A powder type antiperspirant formulation was prepared, using the impalpable powder of EXAMPLE IV, according to the method of EXAMPLE VIII. The formulation included the following:

| | % by weight |
|---|---|
| Blend of Aluminum chlorhydrate, Aluminum chloride, and Urea | 5.00 |
| Dow Silicone 225 | 0.75 |
| Ceraphyl 41 | 0.75 |
| Zinc stearate | 0.15 |
| Bentone 27 | 0.16 |
| Propylene carbonate | 0.06 |
| Perfume | 0.20 |
| Propellant (65% Freon 11, 35% Freon 12) | 92.93 |

EXAMPLE X

A powder type antiperspirant formulation was prepared including the following ingredients:

| | | % by weight |
|---|---|---|
| blend | Aluminum chlorhydrate | 5.62 |
| | Aluminum chloride | 0.38 |
| | Urea | 0.32 |
| | Isopropyl palmitate | 6.41 |
| | Bentone 38 | 0.29 |
| | Propylene carbonate | 0.10 |
| | Zinc stearate | 0.15 |
| | Perfume | 0.20 |
| | Propellant (18% Freon 11, 10% Freon 12, 50% Freon 114, 22% n-butane) | 86.53 |

The Bentone 38 was dispersed in the isopropyl palmitate under mild stirring conditions. The stirring rate was increased to high shear, and the propylene carbonate was added slowly to form a gel. The remaining ingredients, with the exception of the propellant, were added with slow stirring. The propellant was added when the antiperspirant formulation was packaged into aerosol containers.

A sweat test was conducted to determine the efficacy of the antiperspirant of EXAMPLE X. Six weeks prior to the test, the panelists used a mild deodorant having no antiperspirant activity in order to equilibrate the sweat activity of their armpits. During a one week control period during which the panelists used only a mild deodorant, the panelists were subjected to an emotional challenge to produce sweat, and the sweat was collected on sponges placed under the arms. This was done four times during a one week period to obtain an average of the amount of sweat under each arm.

To test the antiperspirant, each panelist used the product antiperspirant under one arm, and a mild deodorant under the other arm. Each product was applied daily, and the sweat reduction was measured 24 hours after the seventh, eleventh, thirteenth and fourteenth days of application. After the sweat is measured, the ratio of the sweat of the test underarm to the sweat of the control underarm is compared to the ratio of sweat under each underarm in the control period in order to measure sweat reduction.

The antiperspirant formulation of EXAMPLE X was tested for sweat reduction, and the results tabulated below:

| Days of Product Use | Sweat Reduction |
|---|---|
| 7 | 45.6% |
| 11 | 52.0% |
| 13 | 50.4% |
| 14 | 55.5% |

EXAMPLE XI

A standard aerosol antiperspirant formulation was prepared from the following ingredients:

| | % by weight |
|---|---|
| Aluminum chlorhydrate | 6.50 |
| Isopropyl myristate | 8.70 |
| Colloidal silica (Cab-O-Sil M5) | 0.43 |
| Perfume | 0.20 |
| Propellant (60% Freon 11, 40% Freon 12) | 84.37 |

This conventional antiperspirant formulation was tested for sweat reduction as described supra, and the results tabulated below:

| Days of Product Use | Sweat Reduction |
|---|---|
| 7 | 29.9% |
| 11 | 35.0% |
| 13 | 34.4% |
| 14 | 28.6% |

Although the additives in the above formulation are not exactly the same as those in EXAMPLE X, it is obvious that the formulation of EXAMPLE X, using the co-spray dried antiperspirant composition of the present invention, gives superior sweat reduction when compared with a typical aerosol antiperspirant formulation.

What is claimed is:

1. An antiperspirant composition prepared by co-spray drying an aqueous solution of a mixture of about 78% to about 92% by weight aluminum chlorhydrate, about 6% to about 12% aluminum chloride and about 1% to about 10% urea.

2. The antiperspirant composition of claim 1 wherein the aluminum chlorhydrate is present in amounts of about 85% to about 90% by weight, the aluminum chloride is present in amounts of about 8% to about 12% by weight and the urea is present in amounts of about 2% to about 7% by weight.

3. An aerosol antiperspirant formulation comprising the antiperspirant composition of claim 1 and a non-toxic, liquefied, normally gaseous propellant.

4. The aerosol antiperspirant formulation of claim 3 wherein the antiperspirant composition is present in amounts of from 2% to about 15%.

5. The aerosol antiperspirant formulation of claim 3 wherein the antiperspirant composition is present in amounts of about 3% to about 8% by weight.

6. The aerosol antiperspirant formulation of claim 4 wherein the propellant is present in an amount of about 60 to 95% by weight and further including about 0.5 to 15% by weight of a vehicle and about 0.1 to 3% of a suspending agent.

7. A composition as defined in claim 1 wherein said mixture has an atomic ratio of Al:Cl of about 1.6:1.

* * * * *